US010767166B2

(12) United States Patent
Kirn et al.

(10) Patent No.: US 10,767,166 B2
(45) Date of Patent: *Sep. 8, 2020

(54) METHODS AND COMPOSITIONS FOR PRODUCTION OF VACCINA VIRUS (71) Applicant: SILLAJEN BIOTHERAPEUTICS, INC., San Francisco, CA (US)

(72) Inventors: David Kirn, Mill Valley, CA (US); John Bell, Ottawa (CA)

(73) Assignee: SILLAJEN BIOTHERAPEUTICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/270,585

(22) Filed: Feb. 7, 2019

(65) Prior Publication Data
US 2019/0169578 A1 Jun. 6, 2019

Related U.S. Application Data (63) Continuation of application No. 15/634,765, filed on Jun. 27, 2017, now Pat. No. 10,202,581, which is a continuation of application No. 14/236,982, filed as application No. PCT/US2012/049550 on Aug. 3, 2012, now Pat. No. 9,719,105.

(60) Provisional application No. 61/515,724, filed on Aug. 5, 2011.

(51) Int. Cl.
*C12N 7/00* (2006.01)
*A61K 35/76* (2015.01)
*C12N 15/86* (2006.01)

(52) U.S. Cl.
CPC .............. *C12N 7/00* (2013.01); *A61K 35/76* (2013.01); *C12N 15/86* (2013.01); *C12N 2710/24132* (2013.01); *C12N 2710/24151* (2013.01)

(58) Field of Classification Search
CPC .............. C12N 7/00; C12N 15/86; C12N 2710/24132; C12N 2710/24151; C12N 2510/02; C12N 7/02; C12N 2710/24143; C12N 2710/24152; C12N 7/025; A61K 35/76; A61K 39/12; A61K 2039/5258; A61P 35/00
See application file for complete search history.

(56) References Cited

U.S. PATENT DOCUMENTS

| 6,267,965 | B1 | 7/2001 | Paoletti et al. |
| 6,761,893 | B2 | 7/2004 | Chaplin et al. |
| 8,574,595 | B2 | 11/2013 | Weggeman |
| 2007/0065411 | A1 | 3/2007 | Kirn |
| 2007/0071769 | A1 | 3/2007 | Sutter et al. |
| 2010/0119552 | A1 | 5/2010 | Hansen et al. |
| 2010/0183672 | A1 | 7/2010 | Kanehara et al. |
| 2010/0215658 | A1 | 8/2010 | Kato |
| 2010/0279386 | A1 | 11/2010 | Chaplin et al. |
| 2012/0230958 | A1 | 9/2012 | Kim et al. |

FOREIGN PATENT DOCUMENTS

| EP | 2085092 A1 | 8/2009 |
| WO | 2008-113078 A1 | 9/2008 |

OTHER PUBLICATIONS

International Search Report of PCT/US2012/049550 dated Nov. 22, 2012.
Manes, N., et al., "Comparative Proteomics of Human Monkeypox and Vaccinia Intracellular Mature and Extracellular Enveloped Virions." Journal of Proteome Research, vol. 7, No. 3, pp. 960-968 (Mar. 2008).
Hwang, Tae-Ho., et al., "A Mechanistic Proof-of-Concept Clinical Trial With Jx-594, a Targeted Multi-Mechanistic Oncolytic Poxvirus, in Patients With Metastatic Melanoma," Molecular Therapy, vol. 19, No. 10, pp. 1913-1922 (Jul. 2011).
Kim, et al., "Systemic Armed Oncolytic and Immunologic Therapy for Cancer with JX-594, a Targeted Poxvirus Expressing GM-CSF," Molecular Therapy, vol. 14, No. 3, pp. 361-370 (Sep. 2006).
ATCC. Converting TCID[50] to Plaque Forming Units (PFU). http://www.atcc.org/Global/FAQs/4/8/Converting%20TCID50% 20to%20plaque%20forming%20units%20PFU-124.aspx. Accessed Feb. 8, 2015. Updated Jul. 25, 2012.
Bleckwenn, N., et al., "Exploring Vaccinia Virus as a Tool for Large-Scale Recombinant Protein Expression," Biotechnol. Prog., vol. 19, No. 1, pp. 130-136 (Jan.-Feb. 2003).
Bleckwenn, N., et al., "Evaluation of Production Parameters with the Vaccinia Virus Expression System Using Microcarrier Attached HeLa Cells," Biotechnol. Prog., vol. 21, No. 2, pp. 554-561 (Mar.-Apr. 2005).
Bleckwenn, N., et al., "Production of Recombinant Proteins by Vaccinia Virus in a Microcarrier Based Mammalian Cell Perfusion Bioreactor," Biotechnol Bioeng., vol. 90, No. 6, pp. 663-674 (Jun. 20, 2005).
Chan, Y., "Preparation of Recombinant Viral Glycoproteins for Novel and Therapeutic Antibody Discovery," Methods Mol. Biol., vol. 525, pp. 31-58 (Feb. 2009).
Coulibaly, S., et al., "The Nonreplicating Smallpox Candidate Vaccines Defective Vaccinia Lister (dVV-L) and Modified Vaccinia Ankara (MVA) Elicit Robust Long-Term Protection," Virology, vol. 341, No. 1, pp. 91-101 (Oct. 10, 2005).
Crouch, N., et al., Cell-Dependent Differences in the Production of Infectious Herpes Simplex Virus at a Supraoptimal Temperature, J. Virol., vol. 9, No. 2, pp. 223-230 (Feb. 1972).
Hikichi, M., et al., "MicroRNA Regulation of Glycoprotein B5R in Oncolytic Vaccinia Virus Reduces Viral Pathogenicity Without Impairing its Antitumor Efficacy," Mol. Ther., vol. 19, No. 6, pp. 1107-1115 (Jun. 2011) (Mar. 8, 2011 published online).
Isayeva, T., et al., "Advanced Methods of Adenovirus Vector Production for Human Gene Therapy: Roller Bottles, Microcarriers, and Hollow Fibers," BioProcessing J., vol. 2, No. 4, pp. 75-81 (2003).

(Continued)

Primary Examiner — Rachel B Gill
(74) *Attorney, Agent, or Firm* — Much Shelist, PC; Christopher M. Cabral (57) ABSTRACT

Certain embodiments are directed to viral production processes for the large scale production of vaccinia virus.

19 Claims, 3 Drawing Sheets (56) References Cited

Kotwal, G. et al., "Growing Poxviruses and Determining Virus Titer," Methods in Molecular Biology, vol. 269, Vaccinia Virus and Poxvirology: Methods and Protocols, pp. 101-112 (Apr. 14, 2004).
Labcompare (CO2 Incubator/Cell Culture Incubator http://www.labcompare.com/General-Laboratory-Equipment/75-CO2-Incubator-Cell-Culture-Incubator (Apr. 16, 2009) Updated 2016.
Life Technologies. Useful Numbers for Cell Culture http://www.lifetechnologies.com/us/en/home/references/gibco-cell-culture-basics/cell-culture-protocols/cell-culture-useful-numbers.html. Accessed Feb. 8, 2015. Updated 2015.
McSharry, J., et al., "Pharmacodynamics of Cidofovir for Vaccinia Virus Infection in an in vitro Hollow-Fiber Infection Model System," Antimicrobial Agents and Chemotherapy, vol. 53, No. 1, pp. 129-135 (Jan. 2009) (Oct. 13, 2008 published online).
RollerCell 40. "RollerCell 40 Overview" and "InVitro Roller Bottles." http://rollercell40.com/rollercell-40.html. Accessed Feb. 8, 2015.
Smith, C., "Incubators: Keeping Your Cells in Style." Biocompare, http://www.biocompare.com/Editorial-Articles/41807-Incubators-Keeping-Your-Cells-In-Style/ (Apr. 4, 2011).
University of Virginia. "DMEM Protocol," http://bme.www.virginia.edu/holmes/downloads/DMEM%20Protocol.pdf (May 25, 2004).
Whitford, W., et al., "Interest in Hollow-Fiber Perfusion Bioreactors is Growing," BioProcess Int., vol. 7, No. 9, pp. 54 (Oct. 23, 2009).
Whitford, W., et al., "The Potential Application of Hollow Fiber Bioreactors to Large-Scale Production," http://www.biopharminternational.com/potential-application-hollow-fiber-bioreactors-large-scale-production (May 2, 2011).
Wikstrom, K., et al., "Clinical Grade Vector Production: Analysis of Yield, Stability, and Storage of GMP-Produced Retroviral Vectors for Gene Therapy," Biottechnol. Prog. vol. 20, No. 4, pp. 1198-1203 (Jul.-Aug. 2004).
Williamson, J., et al., "Argininosuccinate Synthetase-Lyase Activity in Vaccinia Virus-Infected HeLa and Mouse L Cells," J. Gen Virol., vol. 21, No. 2, pp. 349-357 (Nov. 1973).
Bleckwenn et al., Biotechnol. Prog., 21:554-561 (2005.
Schoofs et al., "A high-yielding serum-free, suspension cell culture process to manufacture recombinant adenoviral vectors for gene therapy." Cytotechnology 28:81-89 (1998).
Roth et al., "Using an External Vortex Flow Filtration Device for Perfusion Cell Culture", BioPharm, 10:30-35 (1997).
Roth et al., Vortex Flow Filtration for Cell Separation in Bioreactor Operations, Membrane Separations in Biotechnology, 2nd edition, WK Wang, ed. p. 63-83. N.Y.: Marcell Dekker Inc., 2001.
Jordan et al., "Elements in the Development of a Production Process for Modified Vaccinia Virus Ankara", Microorganisms 1(1):100-121 (2013).

METHODS AND COMPOSITIONS FOR PRODUCTION OF VACCINA VIRUS

CROSS-REFERENCE TO RELATED APPLICATIONS

This application is a continuation of U.S. patent application Ser. No. 15/634,765, filed Jun. 27, 2017 which is a continuation of U.S. patent application Ser. No. 14/236,982, filed Feb. 4, 2014, which is the 35 U.S.C. 371 National Stage of International Application Number PCT/US2012/049550, filed Aug. 3, 2012 and which claims the benefit of U.S. Provisional Application No. 61/515,724, filed Aug. 5, 2011, the entire contents of each of which are incorporated herein by reference.

BACKGROUND OF THE INVENTION

I. Field of the Invention

Embodiments of this invention are directed generally to virology, medicine, and viral therapeutics. Certain embodiments are directed to viral production processes.

II. Background

Oncolytic viruses (OVs) are replicating therapeutics that have been designed or selected to specifically grow in and kill tumor cells. Several groups are in the early stages of commercialization based upon pre-clinical animal models and early clinical data in humans. However, a challenge that still faces the field is to make large scale pharmaceutical grade virus for delivery to patients. Viruses are a biological entity rather than a synthesized drug, thus the manufacturing process involves the production of viruses within cells and the subsequent removal of contaminating cellular debris while maintaining the infective potency. To date, the majority, if not all, commercial manufacturing of vaccinia virus products for human use has been as vaccines in non-human cell cultures. In general for a vaccine application, patients receive low doses of viruses in a local site (often intramuscular) where contaminating cellular proteins may actually serve as an adjuvant to increase the immunogenicity of the preparation. In contrast, for oncolytic virus therapeutics, the doses of viruses needed are up to a million times greater than for vaccine application and may be administered intravenously, intracranially, intraperitoneally or by direct tumor injections. In the case of OVs it is critical to be able to manufacture large quantities of virus which is devoid of contaminating non-human cellular debris. Furthermore, vaccinia viruses are envelope viruses that incorporates host cell protein in the viral membranes. Incorporation of human proteins in the virus envelope will increase its ability to travel without being detected by the human host immune system.

There remains a need for additional methods and composition for large scale oncolytie virus production.

SUMMARY OF THE INVENTION

Vaccinia virus has been produced in HeLa cells grown in suspension culture. However, suspension culture conditions are not presently suitable for large scale production of viruses. Thus, large scale or commercial scale production of vaccinia viruses has not been attempted successfully using HeLa cells. Furthermore, adherent HeLa cell lines were not expected to produce a sufficient number of cells to warrant using adherent HeLa cells to produce vaccinia virus in the quantities needed for large scale production. The current application describes a large scale process for production of vaccinia virus using adherent HeLa cells.

Certain embodiments are directed to methods for producing a vaccinia virus that include one or more of the following steps.

In certain aspects the methods include infecting HeLa cells adhered to a surface with a vaccinia virus by contacting the adherent HeLa cells with a vaccinia virus. Preferably, the vaccinia virus is a recombinant vaccinia virus such as those described at paragraphs [0028] to [0052] of U.S. Patent Application Publication Number 2009/0004723, incorporated herein by reference in its entirety. In certain embodiments HeLa cells adhered to a petri dish are specifically excluded from the scope of the claim. In several embodiments, the present invention provides a method for producing a vaccinia virus comprising (a) infecting HeLa cells adhered to a surface with vaccinia virus (b) culturing the infected cells under conditions permissive for production of progeny virus and (c) harvesting vaccinia virus from the culture.

In some embodiments, methods for producing a vaccinia virus are provided comprising (a) infecting HeLa cells adhered to a surface with a recombinant vaccinia virus by contacting at least $1\times10^7$, $1\times10^8$, $5\times10^8$ $1\times10^9$, $5\times10^9$, $1\times10^{10}$, $5\times10^{10}$, $1\times10^{11}$, $5\times10^{11}$, $1\times10^{12}$, $5\times10^{12}$, $1\times10^{13}$, $5\times10^{13}$ or more adherent HeLa cells, including all values and ranges there between, with a vaccinia virus composition; and (b) culturing the infected cells under conditions permissive for production of 50, 60, 70, 80, 90, 100 or more recombinant vaccinia virus per cell, including all values and ranges there between. Preferably, at least 50 plaque forming units (pfu) vaccinia virus per HeLa cell is produced according to the methods, more preferably at least 75 pfu vaccinia virus per HeLa cell is produced.

In other embodiments, HeLa cells adhered to a surface are infected with vaccinia virus at a multiplicity of infection (m.o.i.) of between 0.001 and 1.0, preferably between 0.005 and 0.5, more preferably between 0.01 and 0.1. In a particularly preferred embodiment, the m.o.i. is between 0.01 and 0.05, including all values and ranges there between. In other preferred embodiments, the m.o.i. is between 0.015 and 0.03. The term "multiplicity of infection" or "m.o.i." refers to the ratio of plaque forming units (pfu) of virus added per HeLa cell during infection.

In related embodiments adhered HeLa cells at density of about $10^4$ to about $10^6$ HeLa cells/cm$^2$, preferably about $10^5$ HeLa cells/cm$^2$ are infected with vaccinia virus according to the methods, wherein the concentration of vaccinia virus is between $10^3$ and $10^5$ pfu/ml, preferably about $10^4$ pfu/ml.

Cultivation of Adherent HeLa Cells.

Adherent HeLa cells for infection with vaccinia virus according to the methods may be cultivated by any suitable method including (but not restricted to) growth in glass and plastic vessels, e.g., culture flasks, bioreactors including without limitation cell factories such as Nunclon® Cell Factories™, cell cubes such as the CELLCUBE® System from Corning Life Sciences, soft plastic bags (like infusion bags) filled with a cell-supporting matrix such as Gibco® or Lampire® cell culture bags; roller bottles; spinner bottles such as Magna-Flex® Spinner Flasks; fermentors; or hollow fibers of various materials such as the cell culture systems from Cellex Biosciences (AcuSyst® hollow fiber reactor), BioVest (Cell-Pharm® System 100 or System 2500) or Fibercell™. Cultivation in bioreactors is preferred as bioreactors allow for precise monitoring and control of variables such as temperature and pH. In certain aspects Cell-Bind™ plasticware (which can be found on the World Wide Web at sigmaaldrich.com) may be used. The cell cultures may be in the form of cell clusters, such as spheroids on a microcarrier bead, or cells on a scaffold (e.g., biodegradable scaffolds), tissue, or tissue organoids. In certain aspects adherent HeLa cells are cultivated in a microcarrier, cell cube, cell factory, T-flask, or roller bottle vessel. In a preferred embodiment, the adherent HeLa cells are cultivated in one or more roller bottles, e.g. using a RollerCell 40 apparatus (Cellon S.A., Luxembourg). The vessel used can comprise, without limitation, a cumulative culture area of about, at least, or at most 1,700; 5,000; 10,000; 25,000; 50,000; 100,000; 150,000; 200,000; 500,000 cm$^2$ including all ranges and values there between. In certain aspects the vessel has a cumulative culture area of at least 168,000 cm$^2$.

The adherent HeLa cells to be infected with vaccinia virus may be cultivated in any suitable culture medium supporting growth, maintenance and attachment to the cell support surface, including without limitation BME (basal Eagle Medium), MEM (minimum Eagle Medium), medium 199, DMEM (Dulbecco's modified Eagle Medium), GMEM (Glasgow modified Eagle medium), DMEM-HamF12 and Ham-F10, Isocove's Modified Dulbecco's medium, MacCoy's 5A medium, or RPMI 1640. Preferably, the culture medium is a defined culture medium. In one aspect, the culture medium is substantially free of serum. Examples of serum free media optimized for use with HeLa cells include, without limitation, VP-SFM (Gibco BRL/Life Technologies), Ex-Cell® HeLa serum free medium (SFM) (Sigma Aldrich), and Quantum 101 (GE Healthcare). In other embodiments, the culture medium may also comprise animal serum such as fetal bovine serum (FBS). For example, the culture medium may comprise 5% to 10% serum (e.g. FBS) or may contain less than 5% serum (e.g. FBS), or any range or value there between. In one embodiment, the culture medium is DMEM supplemented with 5% to 10% FBS, such as 10% FBS.

The term "microcarrier" means a small discrete particle for use in culturing cells and to which cells may attach. Microcarriers may be in any suitable shape, such as rods, spheres, and the like. In many embodiments, a microcarrier includes a microcarrier base that is coated to provide a surface suitable for cell culture. A polypeptide may be bonded, grafted or otherwise attached to the surface coating. Microcarriers have been employed in cell culture for the purpose of providing high yields of attachment-dependent cells. Microcarriers are typically stirred or agitated in cell culture media and provide a very large attachment and growth surface area to volume ratio relative to more traditional culture equipment. See U.S. Patent publication 2011/0027889, which is incorporated herein by reference in its entirety, for a detailed example of a microcarrier.

In certain embodiments the vaccinia virus is a IHD-J, Wyeth, Western Reserve, or Copenhagen strain of vaccinia virus. In certain aspects the vaccinia virus is a recombinant vaccinia virus. The recombinant vaccinia virus can comprise a heterologous coding region. As used herein, a heterologous coding region is a coding region that is not naturally found in vaccinia virus genome. In certain aspects the heterologous coding region can encode an immunostimulatory polypeptide. An immunostimulatory polypeptide can be a cytokine, such as, but not limited to granulocyte macrophage colony stimulating factor (GM-CSF).

In certain aspects the recombinant vaccinia virus selectively replicates in a tumor cell. The recombinant vaccinia virus can comprise a mutation in an endogenous gene. A mutation can be a deletion of nucleic acid sequence, substitution of nucleic acid residues, or insertion of one or more nucleic acid residues that affects the function or expression of a vaccinia virus. The mutation can result in selective growth in a tumor cell or attenuated growth in a non-tumor cell, or enhanced growth in a tumor cell or a combination thereof. A recombinant vaccinia virus comprising a mutation in an endogenous gene can be a thymidine kinase deficient (TK$^-$) vaccinia virus (i.e. a vaccinia virus having a mutation in a gene encoding thymidine kinase that renders the encoded polypeptide nonfunctional). In certain aspects the recombinant vaccinia virus comprising a mutation in an endogenous gene is an IHD-J, Wyeth, Western Reserve, or Copenhagen strain of vaccinia virus; and/or comprises a heterologous coding region. In a further embodiment a vaccinia virus comprising a mutation in an endogenous gene also comprises a heterologous coding region, such as, but not limited to a granulocyte macrophage colony-stimulating factor polypeptide coding region.

Culturing the Infected HeLa Cells.

Adhered HeLa cells that have been contacted with vaccinia virus are cultured under conditions permissive for production of progeny vaccinia virus. Culture conditions can comprise, but are not limited to a defined infection medium, defined pH, defined culture vessel, defined temperature or temperature range, defined cell number, defined cell confluency, defined physical manipulation (e.g, enzymatic or chemical treatment, rotation frequency, shaking speed, etc.), defined gas phase conditions, defined culture time, defined cell seeding density, and defined number of cell passages. In one aspect, the virus may simply be added to the HeLa cell culture medium used to prepare the adherent HeLa cells in which case the culture medium and the infection medium are the same. In other aspects, the culture medium used to prepare the adherent HeLa cells is removed at the infection step and the HeLa cells that have been contacted with vaccinia virus are cultured with an infection medium which may comprise serum or which may be substantially free of serum, until progeny virus is produced Suitable infection media include, without limitation, BME, MEM, medium 199, DMEM, GMEM, DMEM-HamF12 and Ham-F10, Isocove's Modified Dulbecco's medium, MacCoy's 5A medium, or RPMI 1640, any of which may optionally be supplemented with serum. Serum free media such as VP-SFM, Ex-Cell® HeLa serum free medium (SFM)ABBR, and Quantum 101 are also suitable for use as infection medium.

In certain aspects the infected cells are cultured in an infection medium comprising 5-10% serum (e.g. Fetal Bovine Serum (FBS)) at a pH of about 7, 7.2, 7.3, 7.4, 7.5, 7.6, 7.7, 7.8, 7.9, or 8, preferably at a pH above 7.1, more preferably at a pH above 7.2, most preferably at a pH of about 7.3. In other aspects, the cells are cultured in an infection medium comprising less than 5% serum (e.g. FBS) such as 0% serum (e.g. FBS), at a pH of about 7, 7.2, 7.3, 7.4, 7.5, 7.6, 7.7, 7.8, 7.9, or 8, preferably at a pH above 7.1, more preferably at a pH above 7.2, most preferably at a pH of about 7.3. In related aspects, the cells are cultured at a pH of about 7.3 in an infection medium comprising between 0% and 10% serum (e.g. FBS). In other embodiments, the cells are cultured at a pH above 7.2 and below 7.6 in an infection medium comprising between 0% and 10% serum (e.g. FBS). In a preferred embodiment, the infection medium comprises DMEM and optionally 100-300 mM glutamine. Cells can be cultured at a temperature of about 30, 31, 32, 33, 34, 35, 36, 37, 38, 39, or 40° C. In a preferred embodiment, the cells are cultured at a temperature between 36° C. and 37.5° C., preferably at 37° C. In certain aspects the infection medium will specifically exclude one or more of dextran sulfate, Pluronic F-68, Tween-80 and/or soy protein hydrolysate. In preferred embodiments, the infection medium specifically excludes dextran sulfate and at least one of the following components: Pluronic F-68, Tween-80 and soy protein hydrolysate. In other preferred embodiments, the infection medium is substantially free of all of these components.

The methods can further comprising expanding the HeLa cell culture prior to during, or after infection. HeLa cells can be passaged through at least 1, 2, 3, 4, 5, or more culture vessels, e.g., roller bottle culture vessels. In certain aspects the cells are detached from a surface by treating with a detachment solution comprising proteases and/or collagenolytic enzymes, e.g., HyQtase®. Each vessel can have an increased culture area as compared to the previous culture vessel. In certain aspect the culture vessel has a total culture area of at least 84,000 cm to 1,000,000 cm². In certain aspects final passage is to a culture vessel having a culture area of at least 168,000 cm².

In certain embodiments the time interval between seeding of a culture vessel and infection is 12, 24, 48, 72, 96, 120, 144 or more hours, including all values and ranges there between. In certain aspects the adherent HeLa cells are contacted with $1\times10^1$, $1\times10^2$, $1\times10^3$, $1\times10^4$, $1\times10^5$, $1\times10^6$, $1\times10^7$, $1\times10^8$, $1\times10^9$ pfu/mL, including all values and ranges there between, of vaccinia virus. In a preferred embodiment, adherent HeLa cells at density of about $10^4$ to about $10^6$ HeLa cells/cm², preferably about $10^5$ HeLa cells/cm², are contacted with between $10^3$ and $10^5$ pfu/ml of vaccinia virus, more preferably about $10^4$ pfu/ml of vaccinia virus.

In certain aspects the methods include isolating the vaccinia virus produced by the adherent HeLa cells. The harvested vaccinia virus may be concentrated and purified according to methods known to the person skilled in the art. Other embodiments of the invention are directed to a vaccinia virus composition produced by the methods described herein, such as those described at at paragraphs [0295] to [0303] of U.S. Patent Application Publication Number 2009/0004723, incorporated herein by reference in its entirety.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are intended to further demonstrate certain aspects of the present invention. The invention may be better understood by reference to one or more of these drawings in combination with the detailed description of specific embodiments presented herein.

DETAILED DESCRIPTION OF THE INVENTION

Vaccinia viruses are enveloped viruses that produce four infectious forms that differ in their outer membranes: intracellular mature virion (IMV), the intracellular enveloped virion (IEV), the cell-associated enveloped virion (CEV) and the extracellular enveloped virion (EEV). The EEV form is resistant to complement due to host cell incorporation of host regulators of complement activation into the outer EEV membrane (Vanderplassehen et al, (1997) *PNAS* 95:7544-7549). The ability to evade complement inactivation and general ability to evade recognition by host immune system are important features for efficacy in systemic delivery in patients.

The plasma membrane of IMV incorporates numerous host cell proteins during its assembly. Since IMV represents the majority of infectious progeny, producer cells from the same species as the target patients for the oncolytic virotherapy may be advantageous for systemic spread within the patient since the viruses will be less immunogenic. These host cell proteins on the IMV plasma membranes may also provide certain advantages in the infection process.

Although IMV is the majority of the infectious progeny, it has not been definitively established that EEV form of the virus is not contained in the cell culture preparations. The complement activation regulating proteins from the same 
species as the target patients may play a major role in complement activation inhibition and therefore evading immune clearance by the host immune system. Thus, the inventors developed a system to produce large quantities of a vaccinia virus with a human cell component.

Historically, vaccinia virus for use as a vaccine was produced from human scabs, however, subsequently it was grown on the skin of calves, sheep and water buffaloes, in the chorioallantoic membrane of chick embryos or on primary bovine embryo fibroblasts (Ellner, 1998). For the planet-wide concerted effort in smallpox eradication, stocks were produced by infection through scarification of the skin of calves (Fenner, 1977). Virus stocks were prepared from calf lymph and this formulation is the only licensed and available vaccine, known as DRYVAX® (Wyeth). The virus preparation was concentrated and lyophilized, which accounts for its stability (Fenner, 1977). It was produced at a concentration of at least $10^8$ pfu/ml of lyophilized material. It was reconstituted in 50% glycerin and 0.25% phenol in sterile water for injection and delivered to as many as 400 vaccinees intradermally through the use of the bifurcated needle (Fenner, 1977) with a dose at approximately $2.5\times10^5$ pfu—this is at least $10^4$ fold lower than the standard $10^9$ pfu (or higher) dose of vaccinia virus as an oncolytic virus.

A lead clinical candidate for oncolytic vaccinia virus is thymidine kinase inactivated vaccinia virus expressing GM-CSF (Jennerex, JX-594). However, other vaccinia virus variants and strains can also be produced by the methods described herein. For instance JX-963 is a vaccinia virus recombinant that along with removal of the TK gene has an additional deletion of the vaccinia growth factor (VGF) gene constructed on a Western Reserve vaccinia backbone. This double deleted vaccinia virus (vvDD) has been shown to be tumor specific, and have anti-tumor activity in animal models (McCart et al., 2001; Thorne et al., 2007; Naik et al., 2006). A second vvDD variant is JX-929 harbors and expresses the human somatostatin receptor (SSTR2) in infected cells facilitating molecular imaging after systemic delivery using $^{111}$In-pentetreotide (McCart et al., 2004).

I. Cell Culture

Cellular-based viral production has been examined for alternatives to DRYVAX® vaccination and for the production of vaccinia virus use in the field of viral immunotherapy and gene therapy. A second generation vaccinia virus vaccine strain grown in the monkey kidney cell line Vero called ACAM2000 has been developed. In these studies, virus was effectively purified from cellular cultures. In addition, cancer vaccines that employ vaccinia virus in combination with tumor specific antigens (i.e., PSA, CEA) and immunostimulatory molecules (i.e., B7.1, ICAM-1 and LFA-1) have also been produced in cells and administered to patients in Phase I and TI clinical trials (Li, et al., 2005; Guo and Bartlett, 2004). However, in both of these above cases, patients received local rather than systemic administration of viral preparations, and often received a fraction of the total virus dose that are required for oncolytic efficiency in vivo.

In comparison with other viruses that have been put forward as oncolytic virus candidates, poxviruses such as vaccinia represent some unique challenges in large scale manufacture and purification. As some of the largest viruses in nature, poxviruses are visible by light microscopy, and measure 200-400 nm in length (Moss, in Fields' virology B. N. Fields, D. M. Knipe, P. M. Howley, D. E. Griffin, Eds. (Lippincott Williams & Wilkins, Philadelphia, 2001) pp. 2849-2883). Due to its large size, vaccinia virus cannot be sterilized by filtration and thus any manufacturing process is typically closed.

With its entire life cycle occurring within the host cell cytoplasm, the bulk of infectious particles are not released into the cellular medium, but are retained within the infected cell thus purification requires the lysis of the infected cell and the purification of the viral particles from the cellular debris.

In the morphogenesis of poxviruses, they acquire membranes from both de novo membrane synthesis early in morphogenesis, and later acquire additional membranes from the host golgi (Moss, in Fields' virology B. N. Fields, D. M. Knipe, P. M. Howley, D. E. Griffin, Eds. (Lippincott Williams & Wilkins, Philadelphia, 2001) pp. 2849-2883).

The current methods are directed to an adherent cell process developed to produce GMP grade virus for cancer trials. The adherent cell process can be performed in serum free conditions or in the presence of serum. Productivity goals for the manufacturing platform described herein is at least 30, 100, 125, 150, 200 or more pfu/cell—the estimated virus concentration per dose is about $10^9$ pfu/ml.

One embodiment of the invention is directed to procedures for high titer JX-594 production in cell culture. A variety of human cell lines were tested and HeLa, a human cervical cancer cell line, was found to support robust virus replication in adherent cultures. The present methods are not limited to HeLa cells and other adherent cells may be used in the production process, but currently. HeLa cells provide the best mode cell line for production of vaccinia virus.

The typical approach for assessing virus productivity is to perform a standard plaque assay, involving a dilution series followed by a 2-3 day period waiting for plaques to form and then calculation of titer. As an alternative, a quantitative PCR approach (Q-PCR) has been standardized that allows the determination of the number of viral genomes produced following infection. Amplification primers have been optimized that allow us to quantitate the numbers of copies of the viral E9L gene in infected cells and have correlated these results with our standard plaque assay data. The advantage of this approach is that it can be adapted to a 96 well format and the data is available within hours instead of days. Thus the standard initial screen of media and supplements, time to harvest and the affects of concentration of input virus can be rapidly performed and analyzed in 96 well plates. Following this initial screen, all positive "hits" were confirmed with the classic plaque assay.

Components found in commercial serum free media were tested for their affect on virus productivity. The HeLa S3 cell line has been adapted for growth in suspension and in our hands these cells grow as well in EX-CELL™ HeLa Serum Free suspension medium (SAFC Biosciences) as do adherent cells in serum containing media. However as mentioned above, despite excellent cell growth characteristics, the inventors observed very poor virus growth in this medium (less than one virus particle per infected cell). Although the exact formulation of EX-CELL™ HeLa Serum Free medium is proprietary, a known component of this serum free media is sulfated polysaccharide, dextran sulfate, apparently added to help prevent cell clumping. However, dextran sulfate is also known to inhibit the replication of a wide variety of enveloped viruses including retroviruses, herpesviruses, rhabdoviruses and aerenaviruses (De Clercq, 1993). There is approximately 20 mg/L of dextran sulfate in the EX-CELL medium. A variety of concentrations of dextran sulfate were used and assessed in the rapid assay described above. It was found that dextran sulfate did have a dose dependent negative impact on virus productivity, a finding subsequently confirmed using the classical titer assays. While the removal of dextran sulfate does improve virus productivity it is still below the productivity routinely achieved with adherent HeLa cells in serum containing media. Other media components that affect virus productivity include Pluornic F-68, a di-functional, block, co-polymer surfactant that is generally non-toxic to cells; Tween-80, a commonly used detergent; and soy hydrolysate. In certain aspects of the invention the medium will lack one or more of dextran sulfate, Pluronic F-68, Tween-80 and soy protein hydrolysate. Examples of some of these media formulations and serum supplements are outlined in Table 1.

TABLE 1

Culture medium formulations and supplements

| Name of Media | Supplier |
|---|---|
| ExCell HeLa SFM | SAFC |
| ExCell 293 SFM | SAFC |
| OPTIPRO SFM | Invitrogen |
| UltraCulture | Cambrex |
| CHO-S-SFM II | Invitrogen |
| 293 SFM II | Invitrogen |
| VP-SFM | Invitrogen |
| IS-293-V | Irvine Scientific |
| BD Nu Serum replacements | BD Biosciences |

Since vaccinia virus prefers cell to cell contact for efficient spread, it is possible that suspension cell cultures may be limited by poor cell to cell transmission of virus. In certain aspects clumping of the cells can be promoted or cells can be grown on microcarriers or adherent culture can be sufficient for viral production.

In one non-limiting example the following conditions were used for growth of JX-594, which consistently result in titers of over 100 pfu/cell. Cells are set up in roller bottles at $4 \times 10^4$ cells/cm$^2$ and grown for 2 days in culture. At that time, growth media is removed and fresh media containing $10^4$ pfu/ml of JX-594 added. The cells are maintained for an additional 60-70 hours at which time the cells are collected and virus harvested. This set-up can produce approximately 170 doses ($10^9$ pfu/dose) of JX-594. During this process, the inventors discovered factors not anticipated to have had a dramatic effect on viral output. For example, the pH of media has an effect on JX-594 replication. Viral production was optimized in a well buffered media at a pH of 7.3. Productivity from adherent cultures is significantly better than all attempts at suspension cultures.

To ensure the production of high quality viral preparations that are sufficiently free of contaminating products a number of assays can be used for the analysis of virus purity and/or quality. These assays will ensure that viral preparations are comparable to other confirmed lots of virus preparation and ensure the process is successful.

| Characteristic | Method |
|---|---|
| Infectivity titer | Plaque Assay |
| Potency: Cytotoxicity | ED$_{50}$ on U2OS cells |
| Genome titer | qPCR for E9L |
| Total DNA | pico green |
| Host cell DNA, amount | qDNA-PCR |
| Total Protein (ug/mL) | BCA |
| Host cell protein (integral) | ELISA (Cygnus) |

In certain embodiments vaccinia virus can be isolated and purified. The method for purification of Vaccinia virus can include: a. loading a solid-phase matrix with a Vaccinia virus contained in a liquid-phase; b. washing the matrix, and c. eluting the Vaccinia virus.

In certain aspects the matrix can comprise a ligand that binds Vaccinia. The ligand can be attached to the solid-phase matrix by binding or coupling to the matrix. Interaction between the ligand and virus forms a reversible complex, thus, the virus is reversibly retained by the matrix. In certain aspects, glucosamine glycan (GAG), in particular heparan sulfate or heparin, or a GAG-like substance is used as ligand. As used herein, "glycosaminoglycans" (QAGs) are long un-branched polysaccharides consisting of a repeating disaccharide unit.

The ligand can be a biological molecule as, for example, a peptide and/or a lectin and/or an antibody and/or, preferably, a carbohydrate. The ligand may also comprise or consist of sulfate. In a further embodiment, the ligand comprises one or more negatively charged sulfate groups.

In certain aspects the ligand is a hydrophobic molecule as, for example, an aromatic phenyl group, a PPG group, a butyl group, or a hexyl group.

In one aspect, the method comprises purification of Vaccinia virus with hydrophobic interaction chromatography (HIC). In a further embodiment, the method comprises purification of Vaccinia virus with HIC together with affinity chromatography. The use of HIC can provide high virus yields with large reductions in DNA and protein contaminants. The level of DNA contamination can be reduced to 0.01% of the initial starting material and the level of protein contamination can be reduced to below 0.1%.

In certain aspects sulfated cellulose can be used with HIC phenyl column chromatography to yield virus particles at high yields and purity levels.

In certain aspects DNA is degraded or removed prior to or after purification of Vaccinia virus. DNA can be removed by nuclease treatment, such as a Benzonase® treatment. Nuclease treatment reduces the probability of vaccines or viral vectors containing intact oncogenes or further functional DNA sequences.

In related aspects, proteins are degraded or removed prior to or after purification of Vaccinia virus. Proteins can be removed by protease treatment, such as TrypLE™ Select treatment. Preferably, a combination of nuclease and protease treatment is employed to reduce or eliminate contaminating HeLa DNA and proteins.

The matrix can be a gel, bead, well, membrane, column, etc. In a preferred embodiment of the invention, the solid-phase is a membrane, in particular a cellulose membrane. A broad range of modified polymers capable of binding the virus can be used. Examples of such polymers are cellulose derivatives (cellulose esters, cellulose hydrate, cellulose acetate, cellulose nitrate); agarose and its derivatives; polysaccharides such as chitin or chitosan; polyolefines (polypropylene); polysulfone; polyethersulfone; polystyrene; aromatic and aliphatic polyamides; polysulfonamides; halogenated polymers (polyvinylchloride, polyvinyl fluoride, polyvinylidenfluoride); polyesters; homo- and copolymers of acrylnitrile.

Vaccinia virus can be purified under aseptic conditions to obtain an active, stable, and highly pure virus preparation. The Vaccinia viruses can be native or recombinant.

As used herein, "contaminants" cover any unwanted substances which may originate from the host cells used for virus growth (e.g. host cell DNA or protein) or from any 
additives used during the manufacturing process including upstream (e.g. gentamicin) and downstream (e.g. Benzonase).

As used herein, “industrial scale” or “large-scale” manufacturing of Vaccinia virus or recombinant Vaccinia virus comprises methods capable of providing a minimum of 50,000 doses of $1.0\times10^8$ virus particles (total minimum $5.0\times10^{12}$ virus particles) per batch (production run).

As used herein, “Purity” of the Vaccinia virus preparation or vaccine is investigated in relation to the content of the impurities DNA, protein, Benzonase, and gentamicin. The purity is expressed as specific impurity, which is the amount of each impurity per dose (e.g. ng DNA/dose).

As used herein, “Stability” means a measure of how the quality of the virus preparation (Bulk Drug Substance (BDS) or Final Drug Product (FDP)) varies with time under the influence of a variety of environmental factors such as temperature, humidity and lights, and establishes a retest period for the BDS or a shelf-life for the FDP at recommended storage conditions.

The ligand makes possible the elution of the bound Vaccinia virus under such mild conditions that the Vaccinia virus fully retain their biologically activity. This means that virus is infectious. The infectivity of the Vaccinia virus can be preserved during purification such that at least 10%, 20%, 30%, 40%, 50%, 60%, 70%, 80%, or 90% of the initial $TCID_{50}$ (median tissue culture infective dose) is retained during purification. Preferably, at least 30% of the initial $TCID_{50}$ is retained during purification.

In one embodiment, the solid phase matrix is a gel or membrane with a pore size of 0.25 um, preferably of more than 0.25 pm, more preferably of 1.0-3.0 pm demonstrating a linear flow rate under actual purification conditions of 10 cm/min to 20 cm/min. The pore size of the matrix can be 0.25-0.5 μm, 0.5-0.75 μm, 0.75-1.0 μm, 1.0-2.0 μm, 2.0-3.0 μm, or greater than 3.0 μm.

Loading the solid phase with a ligand can be performed by a batch-, column- or membrane approach.

The membrane approach can have some benefits for purification of large viruses like Vaccinia viruses. The large pore sizes and the availability of the ligand on the surface of the membrane allow high binding capacities of even large viral particles.

In one embodiment, the virus is bound to the ligand in ammonium sulphate, for example, at 0.2M, 0.4M, 0.6M, 0.8M, 1.0M, 1.2M, 1.4M, 1.6M, 1.8M, or 2.0M.

When the binding of the Vaccinia viruses or recombinant viruses to the ligand or matrix has proceeded sufficiently, the host cell contaminants (in particular host cell DNA and proteins) that remain in the liquid phase can be removed by washing the matrix to which the Vaccinia virus is bound, with an appropriate washing medium. In one aspect, the matrix is washed with ammonium sulphate at 0.2M, 0.4M, 0.6M, 0.8M, 1.0M, 1.2M, 1.4M, 1.6M, 1.8M, or 2.0M.

The bound Vaccinia viruses or recombinant viruses can be eluted from the matrix. The elution of the captured Vaccinia virus can be performed by agents specifically disrupting the specific interaction between the ligand or matrix and the Vaccinia virus, or by agents non-specifically disrupting the electrostatic interaction between the ligand or matrix and the surface protein. In one aspect, the agent is ammonium sulphate. In a further aspect, the Vaccinia virus can be eluted with GAG or a GAG like ligand. In another aspect, the agent is sodium chloride, more preferably, an increasing NaCl concentration gradient ranging from 0.15M to 2.0M.

Prior to loading on the matrix, a pre-treatment of the virus suspension can be performed, specifically in order to remove contaminants from the Vaccinia virus in the liquid phase culture. Pre-treatment can be one or more of the following steps either alone or in combination: homogenization of the host cells, ultrasound treatment, freeze/thaw, hypo-osmotic lysis, high-pressure treatment, centrifugation, filtration, nuclease treatment, protease treatment, cationic exchange, selective precipitation.

Depending on the agent used for elution of the Vaccinia virus or recombinant virus, post-treatment can be performed to enhance the purity of the virus preparation. The post-treatment could be ultra/diafiltration for further removal of impurities and/or specific or non-specific agents used for elution.

Typically the pH value is increased after elution of the virus, in particular to a pH value of up to 9 or more, in particular to pH 7.5, 7.6, 7.8, 8.0, 8.2, 8.4, 8.5, 8.6, 8.8, 9.0, 9.2, 9.4, 9.5, 9.6, 9.8, 10.0, 10.2, 10.4, or 10.5.

The practice of the invention employs techniques in molecular biology, protein analysis, and microbiology, which are within the skilled practitioner of the art. Such techniques are explained fully in, for example, Ausubel et al. 1995, eds, Current Protocols in Molecular Biology, John Wiley & Sons, New York.

II. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

A variety of human cell lines were tested for production of JX-594. Briefly, adherent HeLa cells, A549 cells, MCF-7 cells, M14 cells, U-2 OS cells, suspended HeLa S3 cells and adherent HeLa S3 cells were infected with JX-594 at a multiplicity of infection of 0.1 and lysates were collected at 72 hours post-infection and the titer of virus determined on U-2 OS cells. The results are illustrated at FIG. 1. Surprisingly good results were obtained in adherent HeLa cells.

Various parameters were examined in an effort to optimize production of virus in adherent HeLa cells. The pH of the infection medium was discovered to have an unexpectedly dramatic effect on viral production (See FIG. 2). Production of JX-594 increased from about 12 pfu/cell at an infection medium pH of 7.1 to about 60 pfu/cell at an infection medium pH of 7.3 under otherwise identical conditions. When the pH of the infection medium was below 7.1, virus production was nearly nonexistent. Further improvements in viral production were observed when the multiplicity of infection was within the range of 0.005 and 0.05, particularly between 0.01 and 0.03 and the when temperature was maintained between 36° C. and 37.5° C. during and post-infection. The use of plastic roller bottles as the adherent surface also contributed to high virus yield.

The presence and amount of serum in the medium used to cultivate the adherent HeLa cells prior to infection was also determined to affect virus yield. Optimal yield was obtained when the medium contained 10% FBS—decreasing the amount of serum in the medium resulted in a corresponding loss of virus yield. Nonetheless, optimization of other parameters (e.g. pH, multiplicity of infection, adherent surface) counteracts the loss of yield attributable to decreased serum concentrations to a degree.

The presence and amount of serum in the infection medium, however, did not substantially affect virus yield. Thus, to obtain surprisingly good yield of vaccinia virus in adherent HeLa cells according to the present invention, the infection medium may comprise serum or may be substantially free of serum.

Figure 1:
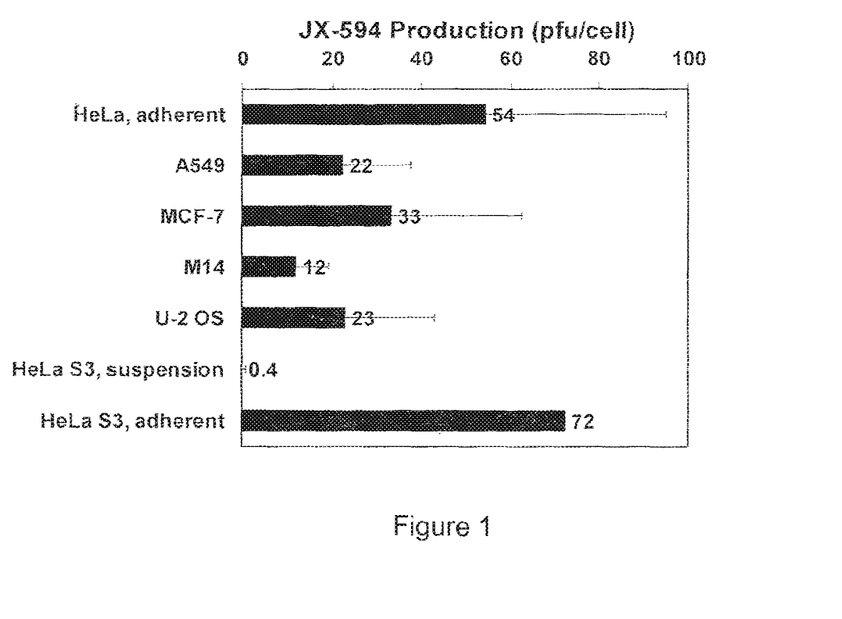
FIG. 1 illustrates production of recombinant vaccinia virus strain JX-594 (pfu/cell) in various human cell lines. Cells were infected at a multiplicity of infection of 0.1 and at 72 hours post infection, lysates were collected and titer determined on U-2 OS cells.
Figure 2:
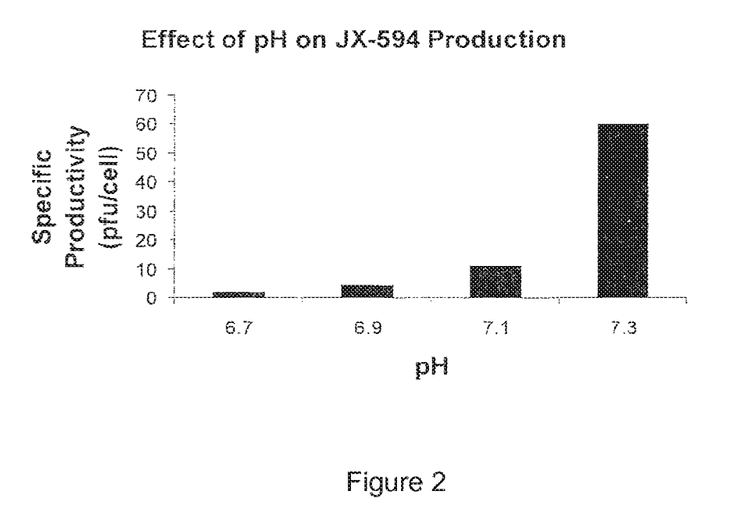
FIG. 2 illustrates the effect of the pH of the infection medium on the productivity of recombinant vaccinia virus strain JX-594 in adherent HeLa cells. Cells were infected at a multiplicity of infection of 0.1 in media of the indicated pH and at 72 hours post infection, lysates were collected and virus titer determined on U-2 OS cells.
Figure 3:
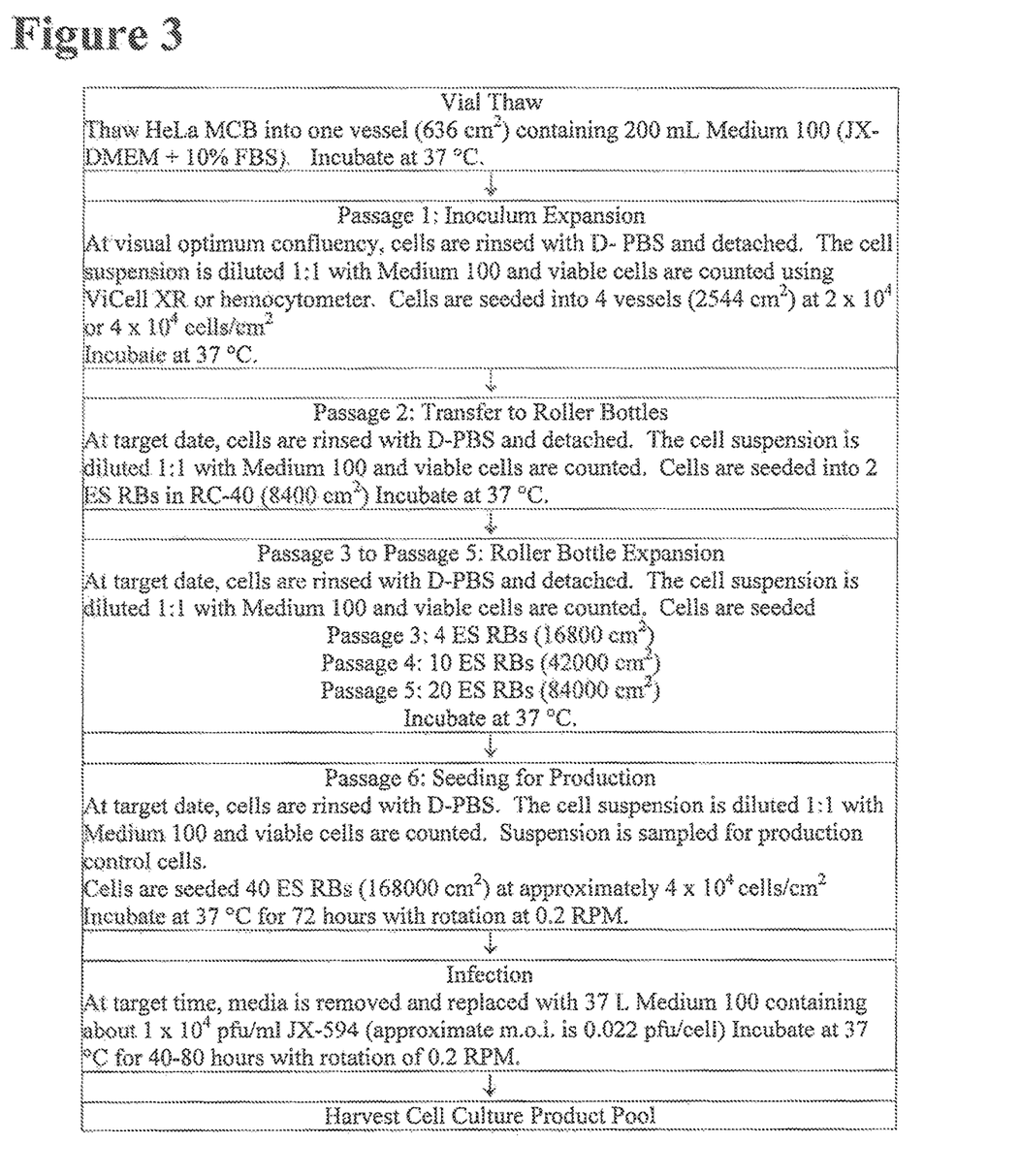
FIG. 3 illustrates an example of the optimized upstream process for production of JX-594.

A flow diagram outlining a non-limiting example of the optimized upstream process is illustrated at FIG. 3.

Vial Thaw and Inoculum Expansion.

The upstream process is initiated by thawing sufficient number of vials from a cell bank. The resulting cell suspension is incubated in a polystyrene cell culture container (636 cm$^2$) (Nunc Nalgene). The cells are grown using a generally applied cell culture protocols to a certain confluency (about 80-95%) determined by visual evaluation In Passage 1, the media is removed, the cells are rinsed with PBS and detached from the culture container. Viable cells are counted using a Vi-Cell XR (Beckman Coulter) or a hemocytometer and then seeded at a density of $1\times10^4$ to $6\times10^4$ cells/cm$^2$ into four polystyrene culture containers (total area 2544 cm$^2$), each containing 200 mL Medium-100. The culture is incubated at 37° C.

If the culture is seeded at $2\times10^4$ then the target date for the next passage is 4 days after seeding. If the culture is seeded at $4\times10^4$ then the target date for the next passage is 3 days after seeding. The process is defined to provide approximately $1\times10^5$ cells/cm$^2$ at the time of each passage.

Roller Bottle Cell Culture Expansion.

On the target date for Passage 2, the media is removed, the cells are rinsed with PBS and detached from the polystyrene culture containers.

The cells are seeded at a density of $1\times10^4$ to $6\times10^4$ cells/cm$^2$ into two Extended Surface (ES) polystyrene roller bottles (RBs, Cellon) in the RC-40 roller bottle apparatus (Synthecon, total surface area 8400 cm$^2$). Each bottle is cultured containing 900 mL of Medium 100 and the cell culture is incubated at 37° C. in an RC-40 Incubator (Sanyo).

On the target date for Passage 3, the cell culture media is removed, the cells are rinsed with PBS and detached. The cell suspension is collected from the ES bottles, mixed 1:1 with Medium 100 and viable cells are counted. The appropriate amount of cell suspension is then seeded into 4 ES RBs (total surface area 16800 cm$^2$) at from $1\times10^4$ to $6\times10^4$ cells/cm$^2$. The cell culture is incubated at 37° C. with 900 mL of media in each bottle.

During Passage 4, the cell culture is transferred to 10 RBs (total surface area 42000 cm$^2$) and during Passage 5, the cell culture is expanded to 20 RBs (total surface area 84000 cm$^2$). Passage 6 is the first critical step of the JX-594 production process as the cell culture is expanded to 40 RBs (total surface area 168000 cm$^2$). The seeding density of the 40 RBs is critical for JX-594 production and has a defined target of $4\times10^4$ cells/cm$^2$. Samples of the cell suspension and conditioned media are collected during Passage 6 for DNA fingerprinting and adventitious agent testing. The temperature of the cell culture during the production seed period is controlled at 37° C.

Infection and JX-594 Production.

The interval from seeding of the 40 RBs to infection with vials of JX-594 from either the Master Virus Bank or Working Virus Bank is a target of 72 hours. On the day of infection, the media is removed from the cell culture and replaced with fresh Medium-100 containing $1\times10^4$ pfu/mL of JX-594 virus. The titer of the infection media is a critical process parameter and has a defined target of $1\times10^4$ pfu/mL. The cell density is not counted at the time of infection but is expected to be at $1\times10^5$ cells/cm$^2$ based on the passage history. The duration of the infection is controlled within the range of 40-80 hours, and is preferably about 44 hours. The temperature of the cell culture during the infection is a critical process parameter and is controlled at 37° C.

Virus titers of up to and even greater than 100 pfu/cell are regularly obtained in accordance with the process JX-594 Downstream Process.

Classical methods for small scale preparation of poxvirus from cells has included hypotonic lysis, followed by rounds of freeze thaw and sonication. The present inventors have discovered that both freeze/thaw and sonication are largely unnecessary steps that often result in decreased virus titers. Accordingly, downstream processing of JX-594 employs nuclease (Benzonase) treatment to digest HeLa DNA and protease (TrypLE™ Select) treatment to digest HeLa protein, followed by tangential flow filtration (TFF). Treatment of crude culture (containing virus and cellular debris in hypotonic lysis buffer) with benzonase resulted in significantly less contaminating host (HeLa) DNA in the preparation. Thus, nuclease treatment combined with TFF provides a significantly purer virus preparation with significantly less contaminating host DNA and protein in the preparation while retaining the infectious titer of the virus. In particular, reduction in DNA contamination from 40 ttg DNA/dose to 3 ug of DNA/dose and reduction in protein contamination from 12 mg protein/dose to 4 mg protein/dose (dose=$1\times10^9$ pfu of JX-594) have been achieved using a combination of nuclease/protease treatment and TFF. Further reductions may be achieved by employing one or more chromatographic steps. In one aspect, the one or more chromatographic steps comprises ion exchange chromatography. In another aspect, the one or more chromatographic steps comprises pseudo-affinity chromatography preferably based on heparin (or heparin-like molecules) or sulfated cellulose, taking advantage of the heparin-binding capacity of the vaccinia virus A27L protein. In yet another aspect, the one or more chromatographic steps comprises membrane adsorption chromatography, e.g. membrane affinity chromatography. Preferred membranes will have a microporous structure with a pore size of at least 3 µM.

REFERENCES

The following references, to the extent that they provide exemplary procedural or other details supplementary to those set forth herein, are specifically incorporated herein by reference.

1. B. Moss, in Fields' virology B. N. Fields, D. M. Knipe, P. M. Howley, D. E. Griffin, Eds. (Lippincott Williams & Wilkins, Philadelphia, 2001) pp. 2849-2883.
2. J. B. Johnston, G. McFadden, Cell Microbiol 6, 695 (August, 2004).
3. C. J. Breitbach et al., Mol Ther 15, 1686 (September, 2007).
4. J. H. Kim et al., Mol Ther 14, 361 (September, 2006).
5. R. M. Buller, G. L. Smith, K. Cremer, A. L. Notkins, B. Moss, Nature 317, 813 (October 31-Nov. 6, 1985).
6. R. M. Buller, G. J. Palumbo, Microbiol Rev 55, 80 (March, 1991).
7. M. Hengstschlager et al., J Biol Chem 269, 13836 (May 13, 1994).
8. T. C. Liu, E. Galanis, D. Kim, Nat Clin Pract Oncol 4, 101 (February, 2007).

9. C. Y. Li, Q. Huang, H. F. Kung, Cell Mol Immunol 2, 81 (April, 2005).
10. J. W. Hodge et al., Front Biosci 11, 788 (2006).
11. P. D. Ellner, Infection 26, 263 (September-October, 1998).
12. F. Fenner, Prog Med Virol 23, 1 (1977).
13. A. W. Artenstein et al., Vaccine 23, 3301 (May 9, 2005).
14. T. P. Monath et al., Int J Infect Dis 8 Suppl 2, S31 (October, 2004).
15. Z. S. Guo, D. L. Bartlett, Expert Opin Biol Ther 4, 901 (June, 2004).
16. E. De Clercq, Adv Virus Res 42, 1 (1993).
17. L. A. Palomares, M. Gonzalez, 0. T. Ramirez, Enzyme Microb Technol 26, 324 (Mar. 1, 2000).
18. B. Horowitz, M. E. Wiebe, A. Lippin, M. H. Stryker, Transfusion 25, 516 (November-December, 1985).
19. M. P. Piet et al., Transfusion 30, 591 (September, 1990).
20. B. H. Chun, Y. Kwon Lee, W. G. Bang, N. Chung, Biotechnol Lett 27, 243 (February, 2005).
21. B. H. Chun, Y. K. Lee, B. C. Lee, N. Chung, Biotechnol Lett 26, 807 (May, 2004).
22. J. A. McCart et al., Cancer Res 61, 8751 (Dec. 15, 2001).
23. S. H. Thorne et al., J Clin Invest 117, 3350 (November, 2007).
24. A. M. Naik et al., Hum Gene Ther 17, 31 (January, 2006).
25. J. A. McCart et al., Mol Ther 10, 553 (September, 2004).
26. A. Piccini, E. Paoletti, Adv Virus Res 34, 43 (1988).
27. C. S. Chung, J. C. Hsiao, Y. S. Chang, W. Chang, J Virol 72, 1577 (February, 1998).
28. A. Karger, B. Bettin, H. Granzow, T. C. Mettenleiter, J Virol Methods 70, 219 (February, 1998).

We claim:

1. A method for producing a vaccinia virus comprising:
   (a) infecting HeLa cells adhered to a cell culture bioreactor surface with a Western Reserve strain vaccinia virus by contacting the HeLa cells with the vaccinia virus at a multiplicity of infection (m.o.i.) of between 0.005 and 1.0 plaque forming units (pfu)/cell;
   (b) culturing the infected cells in an infection medium having a pH of 7.2 to 7.6 at temperature of 30° C. to 40° C.; and
   (c) harvesting vaccinia virus from the culture, whereby at least 50 pfu of vaccinia virus per HeLa cell is produced, calculated as $$\frac{\text{total virus yield from step } (c) \text{ in pfu}}{\text{total number of viable HeLa cells at step } (a)}.$$

2. The method of claim 1, wherein the cell culture bioreactor surface comprises a cumulative culture area of at least 168,000 cm$^2$.
3. The method of claim 1, wherein the pH of the infection medium is 7.2 to 7.4.
4. The method of claim 3, wherein the pH of the infection medium is about 7.3.
5. The method of claim 1, wherein the m.o.i. of step (a) is about 0.01 pfu/cell to about 0.05 pfu/cell.
6. The method of claim 5, wherein the m.o.i. of step (a) is about 0.02 pfu/cell to about 0.03 pfu/cell.
7. The method of claim 1, wherein steps (a) and (b) are performed at a temperature of 32° C. to 37.5° C.
8. The method of claim 7, wherein steps (a) and (b) are performed at a temperature of 32° C., 33° C., 34° C., 35° C., 36° C. or 37° C.
9. The method of claim 1, wherein the density of adhered HeLa cells is between 10$^4$ and 10$^6$ HeLa cells/cm$^2$ during step (a).
10. The method of claim 1, wherein the concentration of vaccinia virus during step (a) is between 10$^3$ and 10$^5$ pfu/ml.
11. The method of claim 1, wherein step (b) is performed for a period of 40-80 hours.
12. The method of claim 11, wherein step (b) is performed for a period of at least 44 hours.
13. The method of claim 1, wherein at least 75 pfu vaccinia virus per HeLa cell is produced calculated as the total virus yield (pfu)/total number of viable HeLa cells at step (a).
14. The method of any claim 1, wherein the medium comprises fetal bovine serum in an amount equal to or less than 10% by volume of the medium.
15. The method of claim 1, wherein the medium does not comprise serum.
16. The method of claim 1, wherein the harvested virus is subjected to one or more purification steps.
17. The method of claim 16, wherein said purification comprises treatment of the harvested virus with a nuclease to remove HeLa cell nucleic acids, and/or a protease to remove HeLa cell proteins, and/or, a tangential flow filtration step, and/or a heparin affinity chromatography step and/or a membrane absorption chromatography step.
18. The method of claim 1, wherein the vaccinia virus is a recombinant vaccinia virus, lacking a functional thymidine kinase gene and/or lacking a functional vaccinia growth factor gene and/or encoding a granulocyte macrophage colony-stimulating factor polypeptide.
19. The method of claim 18, wherein the vaccinia virus lacks a functional thymidine kinase gene and lacks a functional vaccinia growth factor gene.

* * * * *